United States Patent
Wang et al.

(10) Patent No.: US 7,189,888 B2
(45) Date of Patent: Mar. 13, 2007

(54) NONABSORBENT SURGE LAYER HAVING DISCRETE REGIONS OF SUPERABSORBENT AND METHOD FOR MAKING

(75) Inventors: James Hongxue Wang, Appleton, WI (US); Jian Qin, Appleton, WI (US); Jayant Chakravarty, Appleton, WI (US); Fu-Jya Daniel Tsai, Appleton, WI (US); Roland Columbus Smith, Jr., Gainesville, GA (US); Christopher Dale Fenwick, Alpharetta, GA (US); Palani Raj Ramaswami Wallajapet, Neenah, WI (US); D. Keith Osteen, Gainesville, GA (US); Erin A. Evans, Greenville, SC (US); Scott Stephen Englebert, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 339 days.

(21) Appl. No.: 10/036,746

(22) Filed: Dec. 21, 2001

(65) Prior Publication Data
US 2003/0120231 A1 Jun. 26, 2003

(51) Int. Cl.
*A61F 13/15* (2006.01)
*A61F 13/20* (2006.01)

(52) U.S. Cl. .................... 604/367; 604/378

(58) Field of Classification Search ........ 604/367–368, 604/378
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 3,926,891 A | 12/1975 | Gross et al. | |
| 4,062,817 A | 12/1977 | Westerman | |
| 4,071,650 A | 1/1978 | Gross | |
| 4,076,663 A | 2/1978 | Masuda et al. | |
| 4,076,673 A | 2/1978 | Burkholder, Jr. | |
| 4,076,928 A | 2/1978 | Gross | |

(Continued)

FOREIGN PATENT DOCUMENTS

EP 040 087 11/1981

(Continued)

*Primary Examiner*—Michele Kidwell
(74) *Attorney, Agent, or Firm*—Pauley Petersen & Erickson

(57) ABSTRACT

This invention is a surge material having permanent storage properties that results in faster intake and greater saturation capacity and reduced fluid flowback. More specifically the invention is a surge material with a superabsorbent material printed on in a pattern of discrete regions. The objective of the invention is obtained by printing, or other known application process, a liquid superabsorbent precursor solution containing a crosslinkable composition onto a surge material and then curing the printed surge material to crosslink the polymers to get a surge material having discrete regions of superabsorbent material in the surge material. This invention is also useful in making an absorbent core of an absorbent article with improved strength, increased absorbency, and decreased shedding of superabsorbent material.

55 Claims, 14 Drawing Sheets

U.S. PATENT DOCUMENTS

| | | |
|---|---|---|
| 4,079,029 A | 3/1978 | Gross |
| 4,132,695 A | 1/1979 | Burkholder |
| 4,154,898 A | 5/1979 | Burkholder, Jr. |
| 4,286,082 A | 8/1981 | Tsubakimoto et al. |
| 4,310,593 A | 1/1982 | Gross |
| 4,340,563 A | 7/1982 | Appel et al. |
| 4,340,706 A | 7/1982 | Obayashi |
| 4,443,492 A | 4/1984 | Roller |
| 4,500,315 A | 2/1985 | Pieniak et al. |
| 4,573,988 A | 3/1986 | Pieniak et al. |
| 4,670,011 A | 6/1987 | Mesek |
| 5,071,681 A | 12/1991 | Manning et al. |
| 5,147,343 A | 9/1992 | Kellenberger |
| 5,175,046 A | 12/1992 | Nguyen |
| 5,364,382 A | 11/1994 | Latimer et al. |
| 5,411,497 A * | 5/1995 | Tanzer et al. ............... 604/368 |
| 5,487,736 A | 1/1996 | Van Phan |
| 5,490,846 A | 2/1996 | Ellis et al. |
| 5,509,915 A | 4/1996 | Hanson et al. |
| 5,547,747 A | 8/1996 | Trokhan et al. |
| 5,549,928 A | 8/1996 | Trokhan et al. |
| 5,601,542 A | 2/1997 | Melius et al. |
| 5,661,213 A | 8/1997 | Arkens et al. |
| 5,693,707 A | 12/1997 | Cheng et al. |
| 5,788,684 A | 8/1998 | Abuto et al. |
| 5,904,675 A | 5/1999 | Laux et al. |
| 5,938,650 A | 8/1999 | Baer et al. |
| 6,022,610 A | 2/2000 | Phan et al. |
| 6,290,686 B1 | 9/2001 | Tanzer |
| 6,429,350 B1 * | 8/2002 | Tanzer et al. ............... 604/368 |
| 6,610,900 B1 * | 8/2003 | Tanzer ....................... 604/368 |

FOREIGN PATENT DOCUMENTS

| | | |
|---|---|---|
| EP | 108 637 | 5/1984 |
| EP | 188 091 | 7/1986 |
| EP | 192 216 | 8/1986 |
| EP | 206 358 | 12/1986 |
| EP | 208 945 | 1/1987 |
| EP | 729 336 | 6/1998 |
| EP | 0 875 224 A1 | 11/1998 |
| JP | 62062829 | 9/1985 |
| WO | 95/13778 | 5/1995 |
| WO | WO 01/15647 A1 | 3/2001 |
| WO | WO 03/057268 A1 | 7/2003 |

* cited by examiner

NONABSORBENT SURGE LAYER HAVING DISCRETE REGIONS OF SUPERABSORBENT AND METHOD FOR MAKING

FIELD OF THE INVENTION

This invention relates to a surge material useful in an absorbent article for quickly receiving, temporarily storing, and/or transporting fluid. The surge material comprises discrete regions comprising superabsorbent materials. The superabsorbent improves fluid intake and retention, thereby reducing fluid flow back to the skin surface.

BACKGROUND OF THE INVENTION

Conventional surge material is a non-absorbent material used in absorbent articles such as diapers to provide intake of fluid and some temporary storage before fluid is absorbed by an absorbent material or superabsorbent material. Many high-absorbency materials are unable to absorb a liquid at the rate at which liquid is applied to absorbent composites during use. Accordingly, a relatively high concentration of fibrous surge material is desirable to temporarily hold the liquid until the high-absorbency material can absorb it. Conventional surge material is also used to spread the fluid over more surface area of the absorbent material thereby increasing absorbency efficiency.

By providing temporary storage of fluids the surge material keeps the fluid from returning (flowback) through a body-side liner of the diaper, or other absorbent article, and contacting the skin. The surge material increases absorption efficiency and decreases flowback caused by the slower-absorbing absorbent material. Examples of particular surge materials may be found in U.S. Pat. No. 5,490,846 to Ellis et al. and in U.S. Pat. No. 5,364,382 to Latimer.

Conventional surge materials do not include superabsorbent materials. Instead, superabsorbents are commonly used in the absorbent core to increase its absorption capacity. A wide variety of superabsorbent materials are known to those skilled in the art. See, for example, U.S. Pat. No. 4,076,663 issued Feb. 28, 1978 to Masuda et al, U.S. Pat. No. 4,286,082 issued Aug. 25, 1981 to Tsubakimoto et al., U.S. Pat. No. 4,062,817 issued Dec. 13, 1977 to Westerman, and U.S. Pat. No. 4,340,706 issued Jul. 20, 1982 to Obayashi et al.

Methods of applying superabsorbent material onto fibrous absorbent material structures are also known to those skilled in the art. U.S. Pat. No. 6,022,610 issued 08 Feb. 2000 to Van Phan et al. describes the problems that occur in known application methods. For instance, applying a liquid superabsorbent precursor onto a fibrous structure may result in the liquid precursor migrating through the fibrous material. This migration of superabsorbent liquid precursor may result in diminished absorption due to the restriction of the swelling of the superabsorbent material. Gel-blocking may also occur with applied superabsorbent material. Gel-blocking occurs when particles of high-absorbency material deform during swelling and block the interstitial spaces between the particles, or between the particles and absorbent fibers, thus preventing the flow of liquid through the interstitial spaces.

There is a need for surge material with improved intake properties and having permanent storage properties, which can also reduce flowback and leakage of urine, or other fluid, from the absorbent article to the user's skin.

SUMMARY OF THE INVENTION

This invention is a surge material having permanent storage properties that results in greater intake and saturation capacity and reduced fluid flowback. More specifically the invention is a surge material comprising superabsorbent material in a pattern of discrete regions. The invention can be obtained by printing, or applying using another process, a liquid superabsorbent precursor solution containing a crosslinkable composition onto a surge material. Then, the printed surge material is cured to crosslink the superabsorbent polymers, yielding a surge material having discrete regions of superabsorbent material in the surge material.

The invention is useful in an absorbent article such as a diaper. When used in combination with an absorbent composite, the surge material has a high fluid intake and transports the fluid to the absorbent composite. The printed superabsorbent decreases fluid flowback and decreases or eliminates leakage, thereby keeping the user's skin dry. Printing superabsorbent material onto a surge component of an absorbent composite results in increased total absorption capacity.

It is a feature and advantage of the invention to provide an absorbent article having increased fluid intake and absorption capacity.

It is also a feature and advantage of the invention to provide an absorbent article having a wide variety of superabsorbent pattern designs, so that superabsorbent material can be selectively located where it is most beneficial.

It is also a feature and advantage of the invention to provide an absorbent article having increased structural integrity and reduced collapsing of surge and absorbent material layers.

It is also a feature and advantage of the invention to provide a surge material and an absorbent article having increased absorption and absorption under load while retaining flexibility and drapability.

It is also a feature and advantage of the invention to provide a surge material and absorbent composite having increased void volume and reduced or eliminated gel-blocking.

It is also a feature and advantage of the invention to allow the printing of superabsorbent material in various patterns on surge material.

It is also a feature and advantage of the invention to provide a surge material printed with supreabsorbent material from a suberabsorbent precursor solution with good printing resolution of the printed pattern.

The foregoing and other features and advantages will become further apparent from the following detailed description of the presently preferred embodiments. The detailed description is illustrative rather than limiting, the scope of the invention being defined by the appended claims and equivalents thereof.

DEFINITIONS

Figure 1:
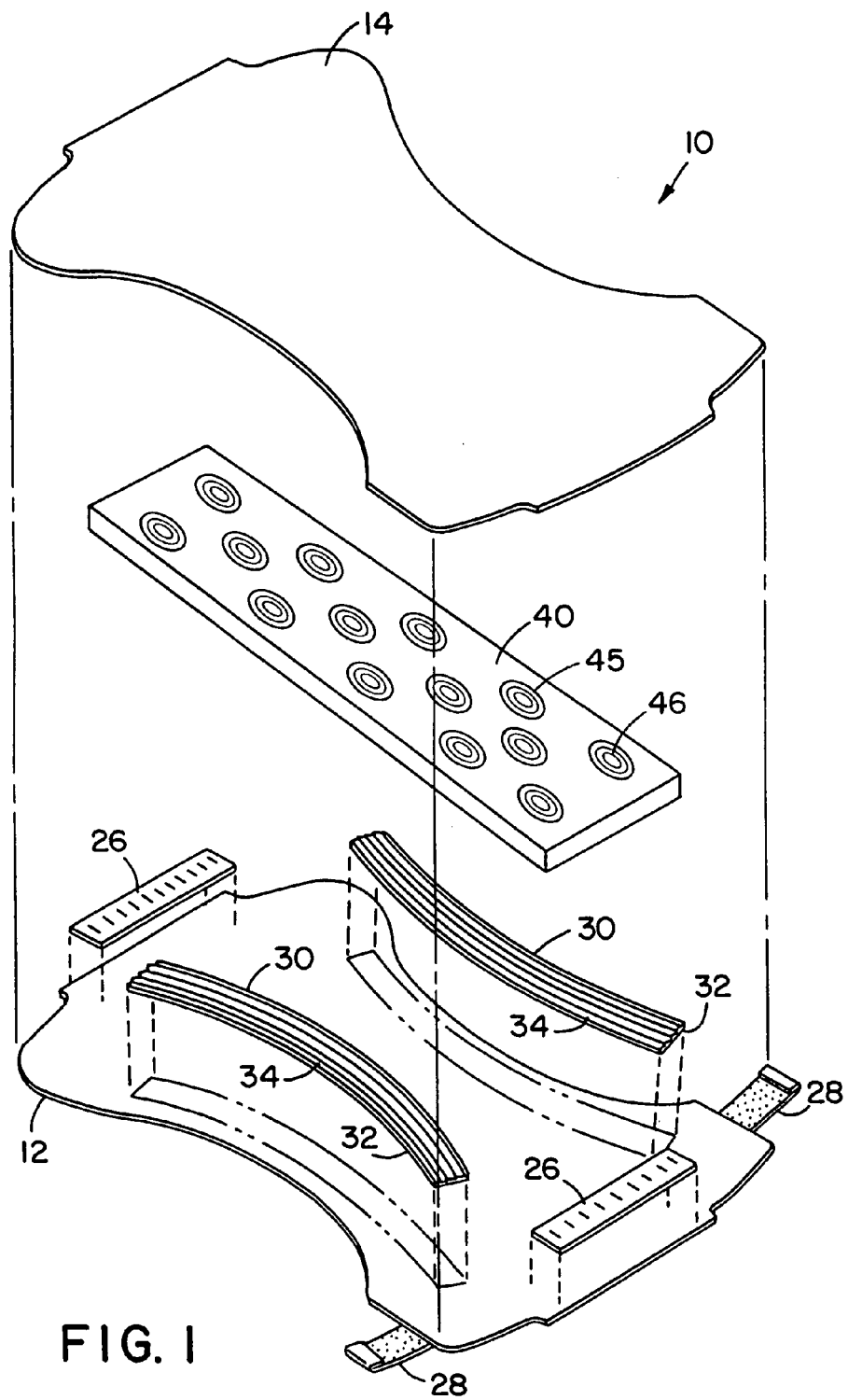
FIG. 1 is an exploded perspective view of an absorbent article, in this case a diaper, according to one embodiment of this invention.

Within the context of this specification, each term or phrase below will include the following meaning or meanings.

"Absorbent article" includes without limitation diapers, training pants, swim wear, absorbent underpants, baby wipes, adult incontinence products, feminine hygiene products, and protective garments including without limitation medical garments, underpads, bandages, absorbent drapes, and medical wipes, as well as industrial work wear garments.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid. The term also includes film-like materials that exist as open-celled foams.

"Gradient" refers to a graded change in the magnitude of a physical quantity, such as the concentration of superabsorbent present in various locations of a surge layer.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than or equal to 90° are designated "nonwettable" or hydrophobic.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Liquid-permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

"Meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Nonwoven" and "nonwoven web" refer to materials and webs of material which are formed without the aid of a textile weaving or knitting process.

"Polymers" include, but are not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic tacticities.

"Spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Superabsorbent material" refers to a water-swellable, water-insoluble organic or inorganic material capable, under the most favorable conditions, of absorbing at least about 20 times its weight, preferably at least about 30 times its weight in an aqueous solution containing 0.9% by weight sodium chloride.

"Surge composite," "surge layer," and "surge material" refer to a material designed primarily to receive, temporarily store, and/or transport liquid in an absorbent article along a mutually facing surface with an absorbent assembly designed to store liquid within the absorbent article.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

This invention is an improved surge layer useful in absorbent articles such as diapers, training pants, swim wear, adult incontinence articles, feminine care products, and medical absorbent products. The surge material has superabsorbent material in discrete regions that increases fluid intake and reduces fluid flowback. The discrete regions can comprise various patterns on the surge layer depending on the needs of the various uses.

FIG. 1 illustrates an exploded perspective view of a disposable diaper. Referring to FIG. 1, disposable diaper 10 includes outer cover 12, body-side liner 14, and surge layer 40 located between body-side liner 14 and outer cover 12. Surge layer 40 includes discrete regions 45 comprising superabsorbent material (SAM) 46. Body-side liner 14, surge layer 40 and outer cover 12 are constructed of conventional non-absorbent materials. By "non-absorbent" it is meant that these materials, excluding any pockets filled with superabsorbent, have an absorptive capacity not exceeding 5 grams of 0.9% aqueous saline solution per gram of material. INDA Standard Test Method IST 10.1 (95), "Standard Test Method for Absorbency Time, Absorbency Capacity, and Wicking Time," published by INDA, Association of the Nonwoven Fabrics Industry, Cary, N.C., herein incorporated by reference, provides the basis for a suitable test method to measure absorbency. The "Absorptive Capacity Test (for small specimens)" may be used to determine the absorbency of a material for the purpose of the subject invention with the following two modifications: (I) IST 10.1 (95) specifies that water is to be used; substitute a 0.9% aqueous saline solution, (ii) IST 10.1 (95) specifies that a 5 gram sample is used. If necessary, a smaller sample, obtained from an absorbent product maybe used instead.

Both the surge layer 40 and body-side liner 14 are constructed from highly liquid pervious materials. These layers function to transfer liquid from the wearer to the absorbent material or superabsorbent material present in diaper 10. Suitable liquid pervious materials include porous woven materials, porous nonwoven materials, films with apertures, open-celled foams, and batting. Examples include, without limitation, any flexible porous sheets of polyolefin fibers, such as polypropylene, polyethylene or polyester fibers; webs of spunbonded polypropylene, polyethylene or polyester fibers; webs of rayon fibers; bonded carded webs of synthetic or natural fibers or combinations thereof. U.S. Pat. No. 5,904,675, issued 18 May 1999 to Laux et al. and incorporated by reference, provides further examples of suitable surge materials. Either layer may also be an apertured plastic film. Suitable batting includes certain air formed thermochemical and chemithermomechanical wood pulps. The various layers of article 10 have dimensions which vary depending on the size and shape of the wearer.

Outer cover material 12 should be breathable to water vapor. Generally outer cover 12 will have a moisture vapor transmission rate (MVTR) of at least about 300 grams/$m^2$-24 hours, preferably at least about 1000 grams/$m^2$-24 hours, more preferably at least about 3000 grams/$m^2$-24 hours, measured using INDA Test Method IST-70.4-99, herein incorporated by reference.

Attached to outer cover 12 are waist elastics 26, fastening tapes 28 and leg elastics 30. The leg elastics 30 comprise a carrier sheet 32 and individual elastic strands 34. The diaper of FIG. 1 is a general representation of one basic diaper embodiment. Various modifications can be made to the design and materials of diaper parts.

Construction methods and materials of an embodiment of a diaper such as illustrated in FIG. 1, are set forth in greater detail in commonly assigned U.S. Pat. No. 5,509,915, issued 23 Apr. 1996 in the name of Hanson et al., incorporated herein by reference. Possible modifications to the diaper illustrated in FIG. 1 are set forth in commonly assigned U.S. Pat. No. 5,509,915 and in commonly assigned U.S. Pat. No. 5,364,382, issued 15 Nov. 1994 to Latimer et al.

Figure 2:
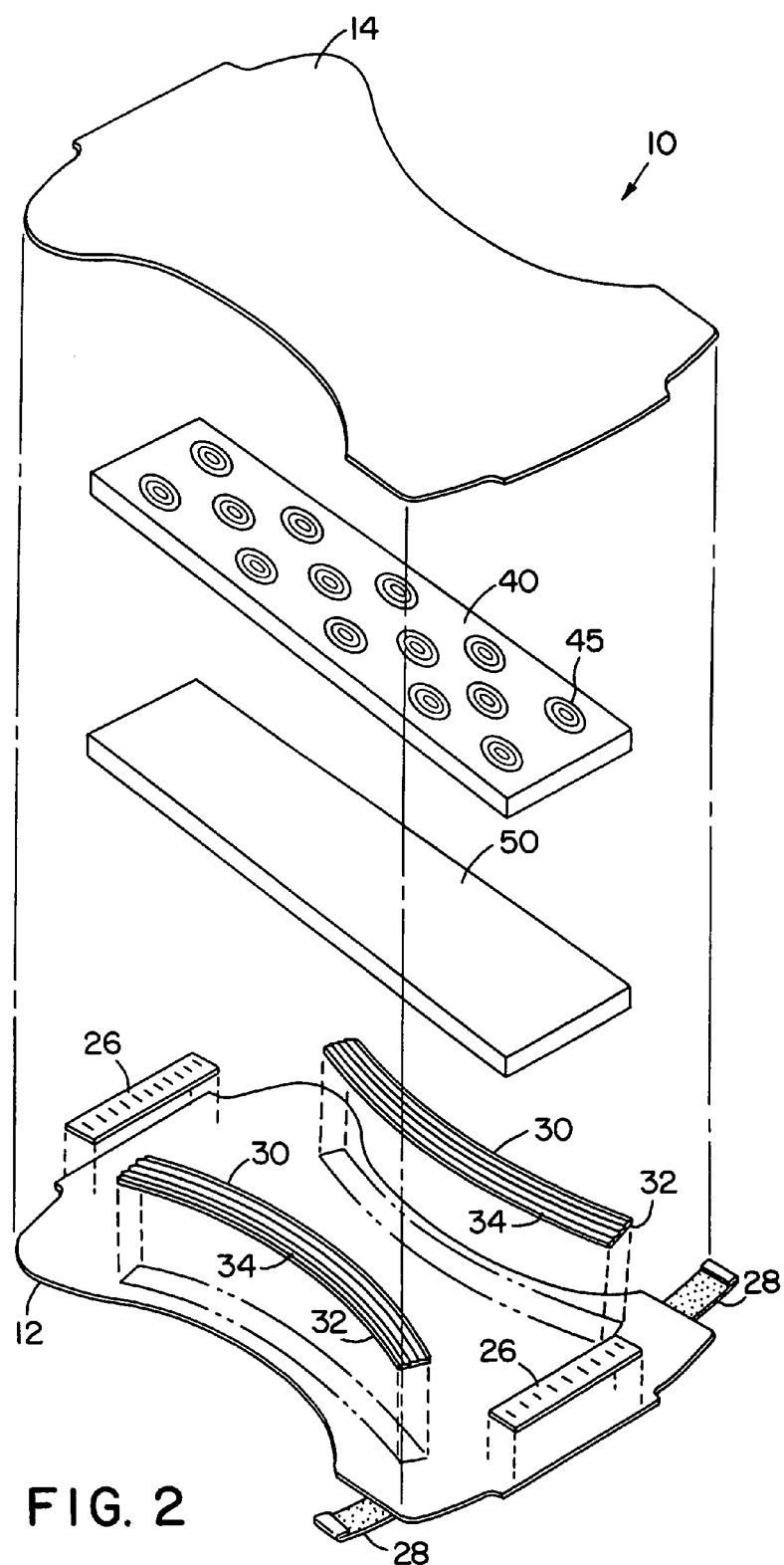
FIG. 2 is an exploded perspective view of a diaper according to one embodiment of this invention.

FIG. 2 illustrates one embodiment of a disposable diaper of the invention. The diaper of FIG. 2 includes absorbent core 50 between the surge layer 40 the substantially liquid-impermeable outer cover 12. Absorbent core 50 typically comprises absorbent materials including natural and wood pulp fibers and nonwoven fibers or webs. "Nonwoven" and "nonwoven web" refer to materials and webs of material which are formed without the aid of a textile weaving or knitting process. Absorbent core 50 typically comprises a matrix of hydrophilic fibers, such as a web of cellulosic fluff, mixed with particles of a superabsorbent material. In a particular embodiment, absorbent core 50 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be non-uniformly mixed. The fluff and superabsorbent particles can also be selectively placed into desired zones of the absorbent core 50 to better contain and absorb body exudates. The concentration of the superabsorbent particles can also vary through the thickness of the absorbent core 50. Alternatively, absorbent core 50 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

Various modifications of diaper 10 of FIG. 2 are possible depending on the needs of the consumer. One embodiment of diaper 10 comprises a barrier tissue between surge layer 40 and absorbent core 50. Alternatively the barrier tissue may be between surge layer 40 and body-side liner 14. A barrier tissue is beneficial in keeping any loosened superabsorbent material from passing through body-side liner 14 and contacting the user.

Surge layer 40 comprises surge material having an operable level of density and basis weight to quickly collect and temporarily hold liquid surges, to transport the liquid from its initial entrance point and to substantially release the liquid to absorbent core 50 and superabsorbent material 46. This configuration can help prevent the liquid from pooling and collecting on the portion of the absorbent garment positioned against the wearer's skin, thereby reducing the feeling of wetness by the wearer. Surge material may have a basis weight of about 0.5 to 10 osy (~15 to 350 gsm), more preferably about 1 to 5 osy (~30 to 150 gsm), and most preferably about 1 to 3 osy (~30 to 100 gsm).

The surge material suitably has a web density ranging from 0.010 grams per cubic centimeter (g/cc) to 0.100 g/cc, or from 0.015 g/cc to 0.075 g/cc, or from 0.020 g/cc to 0.050 g/cc. The range of permeability of the surge material is suitably between 500 and 6000 Darcys, or greater, or between 1000 to 4000 Darcys, or from 1700 to 2500 Darcys.

Various woven fabrics and nonwoven webs having a range of density can be used to construct surge materials. For example, a surge material may be a nonwoven fabric layer composed of a meltblown or spunbond web of polyolefin filaments. Such nonwoven fabric layers may include conjugate, biconstituent and homopolymer fibers of staple or other lengths and mixtures of such fibers with other types of fibers. The surge material also can be a bonded carded web or an airlaid web composed of natural and/or synthetic fibers. The bonded carded web may, for example, be a powder bonded carded web, an infrared bonded carded web, or a through-air bonded carded web. The bonded carded webs can optionally include a mixture or blend of different fibers, and the fiber lengths within a selected web may range from about 3 mm to about 60 mm.

Surge materials may be composed of a substantially hydrophobic material, and the hydrophobic material may optionally be treated with a surfactant or otherwise processed to impart a desired level of wettability and hydrophilicity.

One suitable surge material has a basis weight of about 50 to 100 grams per square meter, and comprises a through-air bonded carded web of a homogeneous blend of 60 percent ESC 233A HR6 3 denier bicomponent fiber including a polypropylene core/polyethylene sheath, commercially available from ES Fibervisions in Athens, Ga., U.S.A., or Type 256 3.0 denier bicomponent fiber including a polyester core/polyethylene sheath, commercially available from KoSa in Salisbury, N.C., U.S.A., and 40 percent Type 295 6 denier polyester fiber, commercially available from KoSa.

Another suitable surge material has a basis weight of about 50 to about 100 grams per square meter, and comprises a through-air bonded carded web of a homogenous blend of 60 percent ESC 215A HR6 1.5 denier bicomponent fiber including a polypropylene core/polyethylene sheath, commercially available from ES Fibervision or Type 256 2.0 denier bicomponent fiber including a polyester core/polyethylene sheath, commercially available from KoSa and 40 percent 3 denier polyester fiber, commercially available from Kosa.

Figure 3A:
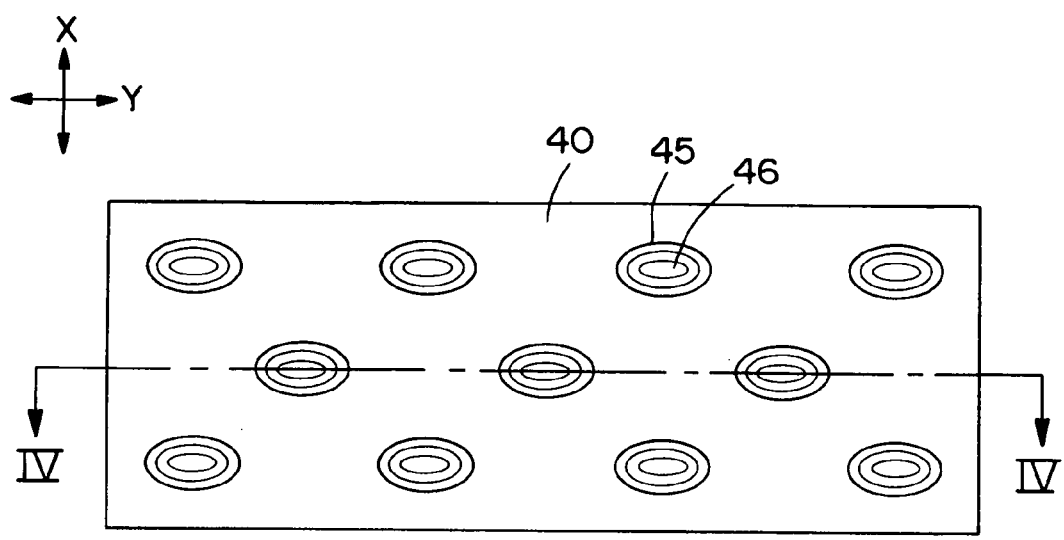
FIG. 3A is a plan view of a surge layer according to one embodiment of this invention.
Figure 3B:
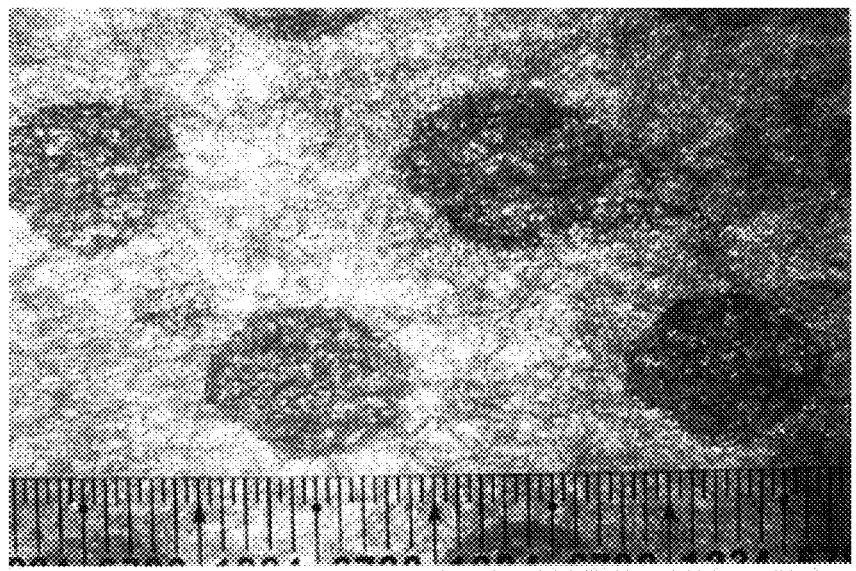
FIG. 3B is a photograph of a plan view of a surge layer according to one embodiment of this invention.

FIG. 3A shows an embodiment of surge layer 40 having a solid dot pattern of discrete regions 45. FIG. 3B is a scanning electron microscope photograph of surge material having the solid dot pattern of discrete regions 45. "Discrete regions" refer to at least one isolated, discontinuous area in the continuous surge material of surge layer 40. The discrete regions define the areas of superabsorbent application in the continuous surge layer. Each discrete region has a surface area on at least one surface of surge layer 40 of at least about 1%. The surface area of a discrete region on at least one surface of surge layer 40 is suitably between about 5 to 80%, and more suitably between about 10 to 70%. The discrete regions comprise superabsorbent material 46 applied to surge layer 40. The discrete regions with superabsorbent material have an absorbency under load of 0.3 psi (pounds per square inch) of at least 5 g/g. The continuous surge material surrounding each discrete region has less absorbency than the discrete regions.

Figure 5:
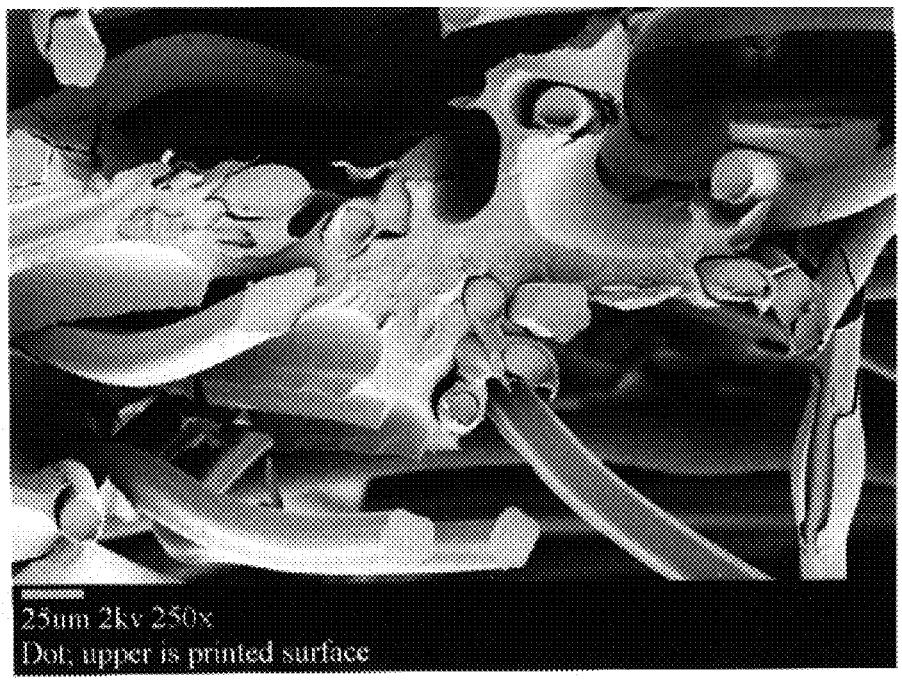
FIG. 5 is a photograph of printed surge material according to one embodiment of this invention.

The discrete regions are an integral part of surge layer 40. The superabsorbent material discrete regions compnse superabsorbent material fused onto the surge fibers in a way similar to steel reinforced concrete. FIG. 5 shows a scanning electron microscope photograph of a discrete region showing the superabsorbent material bonded around the surge material fibers. Discrete regions and superabsorbent material cannot be easily separated from surge 40 by shaking or other movement. The movement of surge layer 40 also does not cause migration (movement of detached superabsorbent material) of superabsorbent material.

Surge material is used in an absorbent article because of its fluid intake and temporary storage properties. It has been discovered that the addition of the superabsorbent material in discrete regions on a surge layer reduces the amount of flowback. "Flowback" refers to the return of fluid back through a surface of the surge layer, or other layer, after it has entered the surge layer through the surface under an external pressure. Flowback in a diaper for instance, results in urine flowing from a diaper or training pant back to the baby's skin. Bonding of the superabsorbent material to the surge material increases the structural strength of the surge layer and has less or no shedding of superabsorbent from the surge material as compared with prior art superabsorbent particles. It has been discovered that the printed superabsorbent material, in the printed discrete regions, functions as a binder material for the surge fibers, thereby reinforcing the fibers and increasing strength and integrity during wearing and handling. The discrete regions of superabsorbent material provide the surge layer with other additional benefits including increased fluid intake, storage, and distribution while retaining the desired flexibility and drapability of the surge layer.

Figure 6:
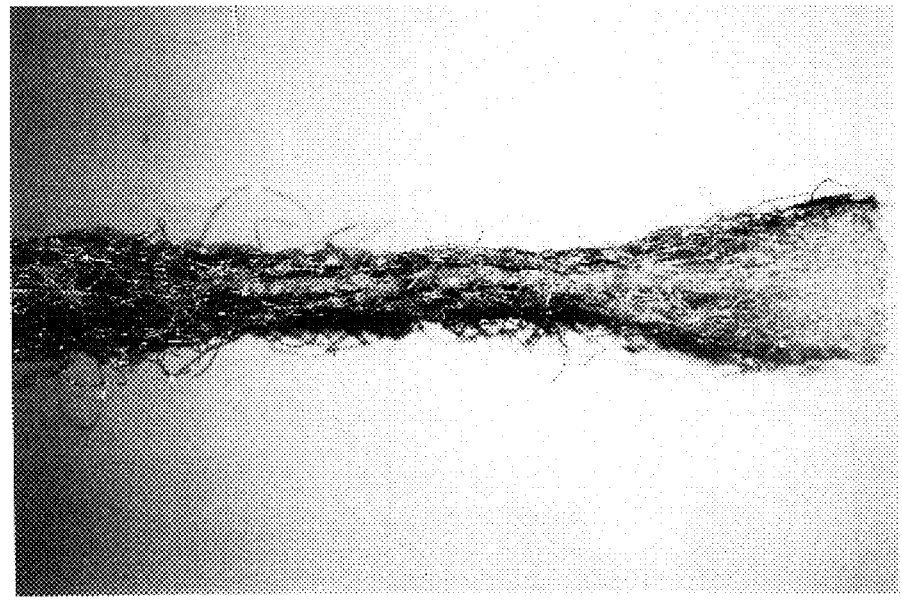
FIG. 6 is a photograph of a discrete region of a surge material before wetted.

Surge layer 40 is substantially uniform in density and flat in an X-Y plane. As shown in FIG. 6, when discrete regions 45 extend through an entire thickness length of surge layer 40, discrete regions 45 preferably have a lower thickness than surge layer 40 before wetting. Discrete regions 45 may also have the same thickness as surge layer 40. The thickness of the discrete regions is suitably about 10% to 95% of the thickness of surge layer 40, more suitably 20% to 90% of the thickness of surge layer 40, and most suitably 30% to 85% of the thickness of surge layer 40. The thickness of unprinted surge layer 40 is suitably about 1 mm to 20 mm, more suitably about 2 mm to 18 mm, and most suitably about 3 mm to 15 mm. The lower thickness of discrete region 45 is due to the application of liquid superabsorbent precursor and subsequent drying causing the evaporation of water and resulting in shrinkage in the thickness direction of the discrete region.

Figure 7:
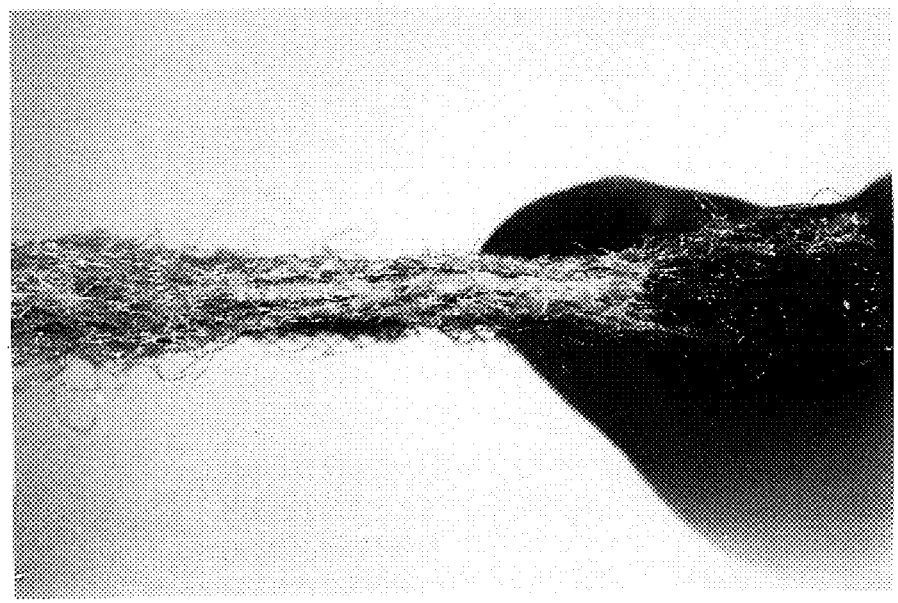
FIG. 7 is a photograph of a discrete region of a surge material after an initial insult of fluid.
Figure 8:
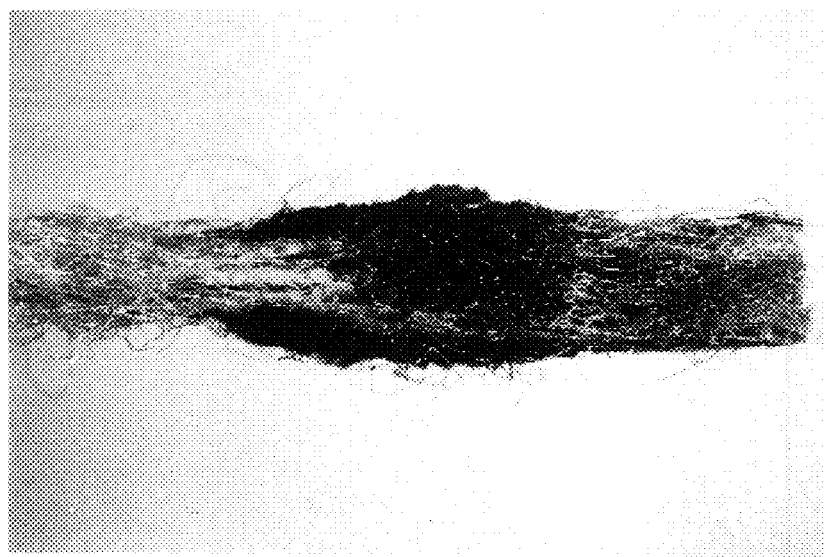
FIG. 8 is a photograph of a discrete region of a surge material partially swollen with fluid.
Figure 9:
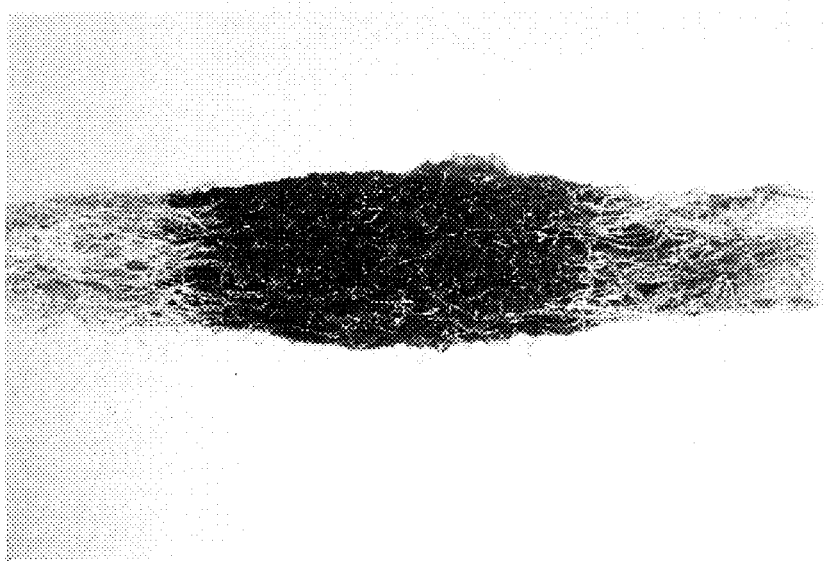
FIG. 9 is a photograph of a discrete region of a surge material fully swollen with fluid.

FIG. 7 shows a discrete region after an initial insult of 0.9% by weight sodium chloride solution, a simulant for unne. The swelling had a delay of about 40 to 50 seconds for solid dot printed surge. Once begun, the swelling continued rapidly. FIG. 8 shows a partially swollen discrete region and FIG. 9 shows a fully swollen discrete region. As shown in FIGS. 7–9 discrete regions 45 swell in a thickness direction due to the absorbent capacity of the superabsorbent material. The swelled thickness of the discrete regions is at least about 1.25 times the dry thickness, more suitably at least about 1.5 times the dry thickness, and most suitably at least about 2 times the dry thickness. The swelling rate can be increased by making the surface of the printed superabsorbent material wettable by applying a surfactant or mixture of surfactants. An example of a useful surfactant is AHCOVL™.

Superabsorbent material 46 is preferable applied to surge layer 40 by printing. A wide range of printing methods well known in the art, such as screen printing or the gravure printing process, are applicable for printing superabsorbent material on nonwoven materials according to this invention. Other known application processes include, without limitation, spraying or dipping. A wet superabsorbent precursor solution is printed on surge layer 40 in a predetermined, desired configuration resulting in discrete regions 45. The superabsorbent precursor is crosslinked after application to bind the superabsorbent to the surge material and form discrete regions 45. In one embodiment a preferred amount of superabsorbent added is about 1% to 400% add-on level, more suitably about 5% to 300% add-on level, and most suitably about 10% to 200% add-on level. "Add-on level" is defined as the dried, crosslinked superabsorbent weight as a percentage of the weight of the surge material. For example, 0.4 g of superabsorbent material added to 1.0 g of surge material comprises 40% add-on level.

Discrete regions 45 can be applied to surge layer 40 in various locations and patterns which can be configured according to the needs of different absorbent articles. Suitable discrete regions 45 have a surface size that places about 0.1 to 10 discrete regions per square centimeter, more suitably about 0.2 to 8 discrete regions per square centimeter, and most suitably 0.4 to 6 discrete regions per square centimeter. Suitably a percentage of at least one surface of surge layer 40 has a surface area covered by discrete regions 45 is about 1% to 50%, more suitably about 10% to 45%, and most suitably about 15% to 40%. Discrete regions 45 can also comprise various shapes such as, without limitation, circles, ovals, triangles, straight or curved bars, and rings.

In one embodiment of this invention, superabsorbent material 46 is printed, or otherwise applied, in discrete regions on absorbent core 50. Printing superabsorbent material 46 onto absorbent core 50 provides a binding effect, enhancing strength of the absorbent core, especially when wet. The additional printed superabsorbent material 46, according to this invention, on absorbent core 50 also provides the advantages of more absorbency and less shedding of superabsorbent material.

Figure 4:
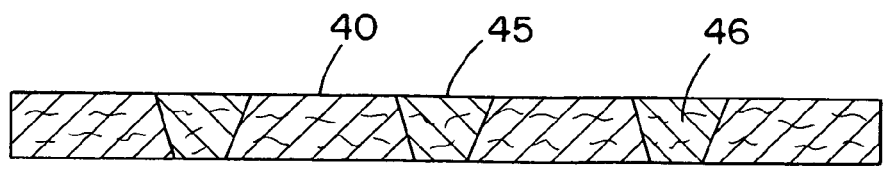
FIG. 4 is a sectional view of a surge layer according to one embodiment of this invention.

FIG. 4 shows a cross sectional view of surge layer 40. FIG. 4 shows discrete regions 45 comprising a depth extending through a thickness of surge layer 40. When discrete regions 45 comprise a depth extending through the thickness of surge layer 40 the superabsorbent material 46 in discrete region 45 also extends through the thickness of surge layer 40. In another embodiment discrete regions 45 comprise a depth that may only partially extend through the thickness of surge layer 40 creating a surge layer which has a first surface with discrete regions 45 and a second surface with no discrete regions. This embodiment is beneficial in that discrete regions 45 can face away from the absorbent article user thereby keeping the superabsorbent and any absorbed fluids away from the user. Discrete regions 45 may also extend through various depths of surge layer 40. Controlling the depth of discrete regions 45 allows for additional selectivity in applying superabsorbent depending on the needs of the absorbent article.

In one preferred embodiment discrete regions 45 comprises a gradient of superabsorbent material extending through surge layer 40. The gradient of superabsorbent material refers to the cone shaped printed pattern that occurs as the discrete region extends through the thickness direction of the surge layer. The cone shaped gradient can vary as to specific size. FIG. 4 shows discrete regions 46 as one embodiment of conical discrete regions. A conical discrete region allows superabsorbent to extend through surge layer 40 and, when the tip of the cone extends toward the absorbent article user, may be used to keep the swelling superabsorbent away from the user.

Preferred superabsorbent materials allow for creating well defined discrete regions with little or no migration of the liquid superabsorbent precursor through the surge material and little or no smearing during printing. It has been discovered that certain polymer parameters, such as molecular weight control, control and defining the optimal solution rheology, solid content of the superabsorbent precursor solution, neutralization level of the superabsorbent precursor, printing methods, and combinations of these, are the key factors in designing a superabsorbent material that provides the desired printing characteristics.

Figure 10:
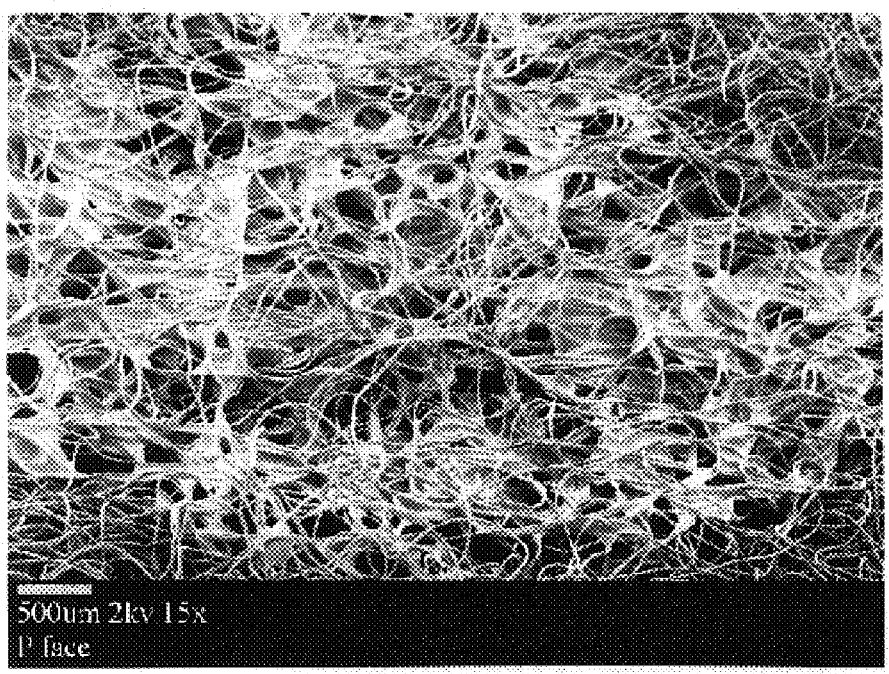
FIG. 10 is a photograph of a surface of a discrete region of a surge material according to one embodiment of this invention.
Figure 11:
FIG. 11 is a photograph of a cross sectional view of a surge material according to one embodiment of this invention.

FIG. 10 shows the surface of one of discrete regions 45 at a magnification of 15× by scanning electron microscopy. FIG. 10 shows a porous web of surge material fibers. The pores penetrate the thickness of surge layer 40 and allow liquid to flow through surge layer 40 through the open and interconnected capillaries between the fibers and printed discrete superabsorbent regions. FIG. 6 shows a cross-sectional view of a surge layer 40 magnified 30× by scanning electron microscopy. The side of FIG. 11 marked printed side shows a cross section of a discrete region and the superabsorbent printed surge material. FIG. 11 shows the discrete regions are porous in the X-Y plane providing channels for incoming liquid to flow through the thickness direction. The superabsorbent in the discrete region forms a layered structure. The layers of superabsorbent material act as a mortar-like material between the surge material fibers thereby increasing strength, especially when wet. In between the layers of superabsorbent material are layers of voids. The voids create channels in the X-Y plane that allow for improved liquid intake and distribution along the X-Y plane through a broader area and then to the absorbent core layer beneath the surge layer and substantially reduce or eliminate gel-blocking. FIGS. 6–9 show a sequential swelling of a discrete region. After wetting the superabsorbent material swells and, as seen in FIGS. 6–9, causes the discrete region to swell and increase in thickness as well. The voids in the discrete regions may also expand during swelling and thereby increase fluid handling of the surge layer.

Figure 12:
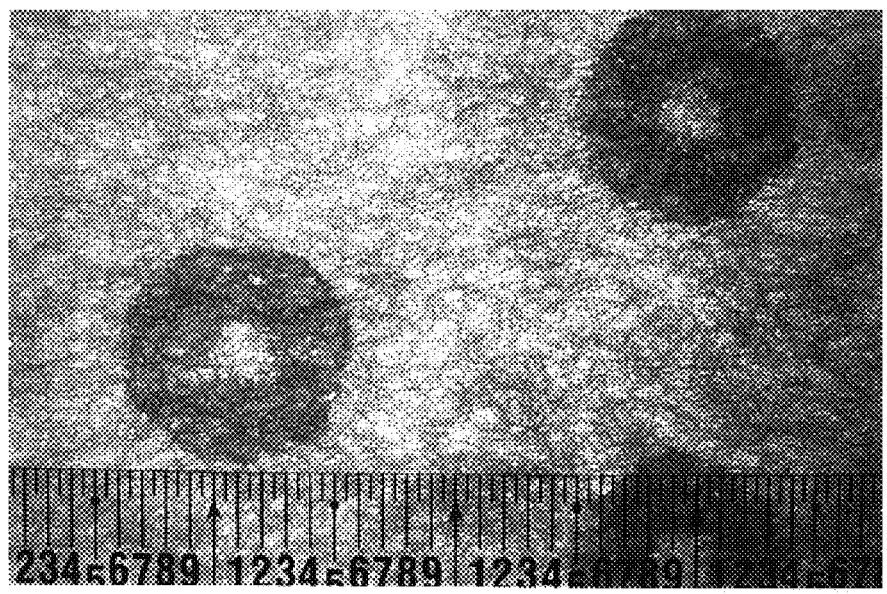
FIG. 12 is a photograph of printed surge material according to one embodiment of this invention.
Figure 13:
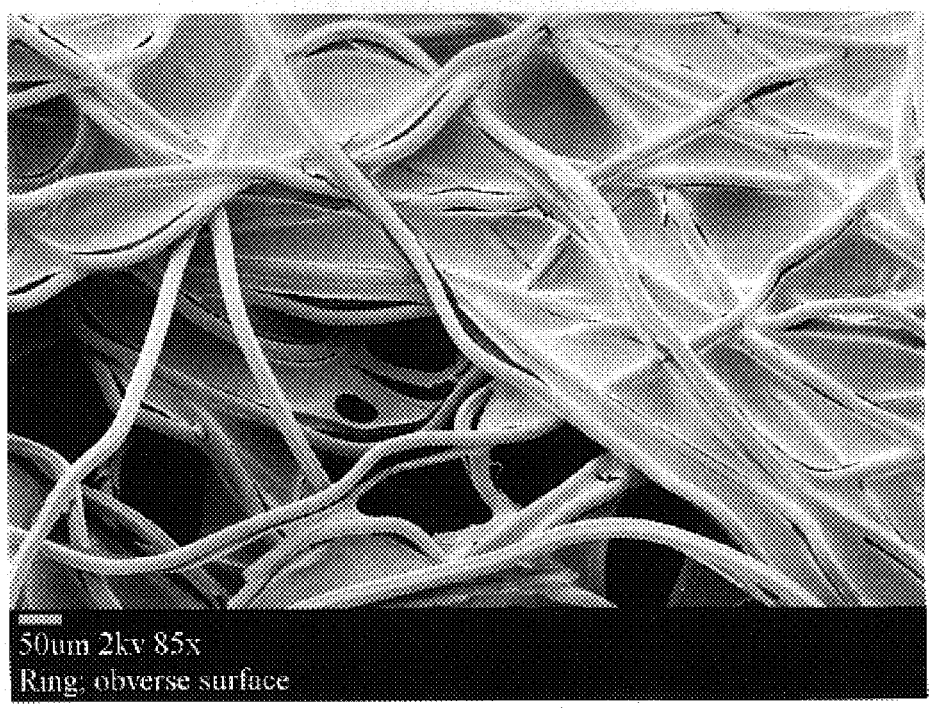
FIG. 13 is a photograph of printed surge material according to one embodiment of this invention.
Figure 14:
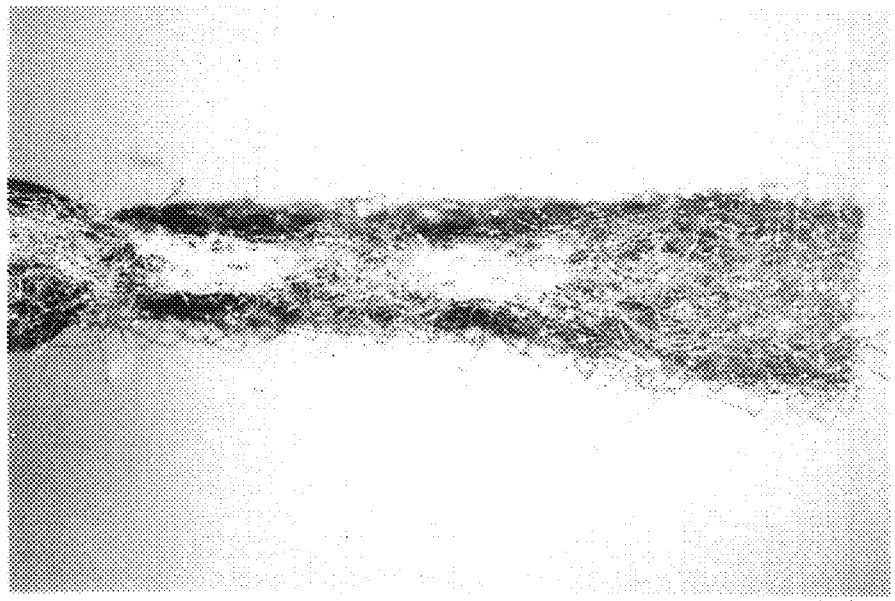
FIG. 14 is a cross-sectional photograph of printed surge material according to one embodiment of this invention.
Figure 15:
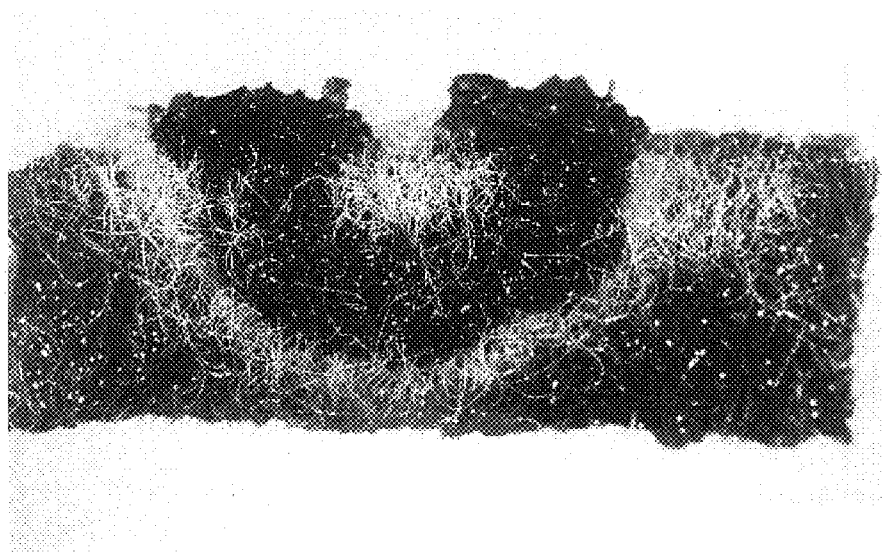
FIG. 15 is a photograph of printed surge material according to one embodiment of this invention.

Discrete regions of this invention can comprise various shapes and sizes. FIG. 12 is a scanning electron photograph of one embodiment of this invention showing the discrete regions are in a ring shape. In the center of the ring-shaped discrete region is surge material without superabsorbent material. FIG. 13 shows a close up of one ring-shaped discrete region showing the superabsorbent material bonded to the surge material fibers. FIG. 14 shows a cross-section of a ring-shaped dicrete region while dry. The ring-shaped discrete region is thinner than the surrounding surge material because of the printed superabsorbent material. FIG. 15 shows a ring-shaped discrete region after wetting. The discrete region has swollen due to the absorption of water. The center of the ring contained substantially no superabsorbent material and, as seen in FIG. 15, does not swell when wetted.

To obtain the different shaped discrete regions, different shaped printing screens can be used. One such screen can have a solid dot pattern. In one embodiment, the screen for the ring pattern had an outer ring diameter of 8 millimeters and an inner ring diameter of 4 millimeters. The inner and outer rings can be in-line or offset patterns. A tray with silk screen with the un-patterned areas blocked can be used for printing. Only the patterned areas allowed the liquid superabsorbent precursors to pass through. A sufficient amount of the liquid superabsorbent precursor is added onto the screens. The liquid precursor is spread with a roller or a soft rubber bladed squeegee. Depending on the time and pressure, either a completely or partially penetrated printed surge is obtained. After printing the resulting surge is dried in a well-vented hood or in an oven at a temperature such as 60° C. overnight to remove moisture. It is subsequently cured at a temperature such as 120° C. for about 4 hours to produce a surge printed with superabsorbent.

Superabsorbent material 46 is made from a superabsorbent precursor solution. In one embodiment a preferred superabsorbent precursor is a hydrolyzed copolymer of an $\alpha$-olefin with one of an $\alpha,\beta$-ethylenically unsaturated organic acid anhydride and ester. The $\alpha$-olefin preferably comprises 3 to 20 carbon atoms, and in one embodiment the preferred $\alpha$-olefin monomer is isobutylene. Other suitable $\alpha$-olefin monomers include propylene, 2-methyl 1-butene, 2-ethyl 1-butene, 2,4, dimethyl pentene, and any olefin with electron donating groups such as alkyl, cycloalkyl, alkoxy, amino groups, etc. The unsaturated acids include, but are not limited to, fumaric acid and esters and maleic anhydride and esters. A preferred copolymer is a neutralized hydrolyzed copolymer of isobutylene and maleic anhydride. Such a copolymer is available from Kuraray America, Inc. (New York, N.Y.) under the trade name ISOBAM™. ISOBAM™ is available with molecular weights ranging from about 5,500–350,000 g/mol. ISOBAM™ can be neutralized by adding ISOBAM™ powder to an alkaline solution of sodium hydroxide or ammonium hydroxide for 4 to 5 hours at 90° C. to 100° C.

A nonpolymerizable latent crosslinker can be added to the neutralized ISOBAM™ solution. Possible nonpolymerizable latent crosslinkers include polyols, polyamines, or polyepoxy compounds. Examples include, without limitation, ethylene glycol, diethylene glycol, triethylene glycol, polyethelene glycol, polyvinyl alcohol, polyethylele oxide, glycerol, 1,3-propanediol, 1,4-butanediol, 1,5-pentanediol, 1,6-hexanediol, 1,8-octanediol, 1,1,1-trimethylolpropane, 1,4-butanediamine, 1,5-pentanediamine, 1,6-hexanediamine, diethylenetriamine, and analogs and derivatives thereof or any compound having functional groups that react with carboxyl groups such as amino, hydroxy, epoxy, etc. Polyvalent metal ions are also useful crosslinkers. Examples include $Al^{3+}$, $Zr^{4+}$, $Fe^{2+}$, $Fe^{3+}$, $Ca^{2+}$, $Ti^{3+}$, and $Cr^{3+}$. Crosslinking density in the resulting superabsorbent composition is determined by the amount of nonpolymerizable latent crosslinker present. For low temperature crosslinking, which is less likely to melt surge material fibers, a polyamide crosslinker is preferred.

The amount of crosslinkable component preferably ranges from about 0.25% to about 15% by weight based on the dry weight of superabsorbent material precursor to be crosslinked. Higher amounts of crosslinking components usually leads to higher crosslinking density and a lower molecular weight ($M_c$) between the crosslinks. More preferably the amount of crosslinking component is in a range from about 1% to about 8% by weight. Most preferably the amount of crosslinking component is in a range from about 1% to about 5% by weight. The concentration of the copolymer in water is preferably in the range of about 15% to about 50%. Viscosity of the solution depends upon the molecular weight of the polymer in solution. Using a higher concentration of a lower molecular weight polymer will result in a suitable solution for printing onto the surge material.

Furthermore, the superabsorbent material may include hydrolyzed partially neutralized starch acrylonitrile graft copolymers, partially neutralized starch acrylic acid graft copolymers, partially neutralized saponified vinyl acetate-acrylester copolymers, hydrolyzed acronitrile copolymers, carboxymethyl cellulose, carboxymethyl starch, chitosan salts, partially neutralized polyaspartic acid, polyquartenary ammonium salts, polyvinyl amines, polyethylene imines, or combinations of any of these.

Another preferred superabsorbent precursor material is a linear neutralized polyacrylic acid. "Linear" means the polyacrylic acid precursor is substantially unbranched in structure. "Neutralized" means that the carboxyl acid groups of the precursor molecule are neutralized to their salt equivalents using a base such as sodium hydroxide, sodium carbonate, or other hydroxide. Suitable linear neutralized polyacrylic acid is 40% to 90% neutralized, more suitably 45% to 85% neutralized, and most suitably 50% to 80% neutralized.

The polyacrylic acid superabsorbent precursor solution can contain a linear polyacrylic acid with latent nonpolymerizable crosslinkers or a copolymer of acrylic acid and a latent polymerizable crosslinker such as aminopropyl vinyl ether or ethylene glycol vinyl ether. Possible latent nonpolymerizable crosslinkers include, without limitation, $\alpha,\beta$-ethylenically unsaturated comonomers having an additional functional group including, for example, hydroxy, amino, and epoxy groups. Examples of latent polymerizable crosslinkers include, without limitation, ethylene glycol allyl ether, 2-hydroxyethyl methacrylate, polyethylene glycol methacrylate, ethylene glycol vinyl ether, and aminopropyl vinyl ether of any compound having an $\alpha,\beta$-ethylenically unsaturated group and one or more functional groups which react with a carboxyl group such as amino, hydroxy, epoxy, etc. Examples of the latent nonpolymerizable crosslinker include, without limitation, polyfunctional alcohols, polyfunctional amines, polyfunctional alcohols and polyfunctional amines on the same molecule, and mixtures thereof. Examples of these latent nonpolymerizable crosslinkers include, without limitation, ethylene glycol, diethylene glycol, triethylene glycol, polyethylene glycol, glycerol, polyethylene oxide, polyvinyl alcohol, 1,1,1-trimethylolpropane, 1,3-propanediol, 1,4-butanediol, 1,5-pentanediol, 1,6-hexanediol, 1,7-heptanediol, 1,4-butanediamine, 1,5-pentanediamine, 1,6-hexanediamine, diethylene triamine and their analogs or homologs, and any compound or chemical having functional groups that react with carboxyl acid groups, such as amino, hydroxy, and epoxy groups, etc.

Superabsorbent material 46 can comprise two or more superabsorbent precursors. When used in combination the ratio of the first superabsorbent precursor to the second superabsorbent precursor can be between 99:1 to 1:99. Suitably the percentage of the first superabsorbent precursor is about 10% to 90%, and most suitably about 30% to 70%. The advantages of using two superabsorbent precursors in combination include providing complimentary absorbent properties, wettability, complementary liquid wicking properties, and other desirable properties.

Unlike current commercial superabsorbents based on copolymerized neutralized polyacrylic acid, crosslinking of superabsorbent material 46 of this invention occurs after printing of superabsorbent material 46 onto the surge material. Crosslinking of the superabsorbent precursor polymers can be done by heat curing. Alternative crosslinking methods include exposing the polymers to microwaves or electrobeam radiation. These alternative methods are much quicker than heat curing.

EXAMPLES

Numerous samples of superabsorbent materials were prepared according to this invention. Table 1 shows a representative sample of superabsorbent material solutions used in the following described tests and printed on surge material examples to show the benefits of the invention. Each printable superabsorbent solution of Table 1 has a diethylenetriamine latent crosslinker of 4% by weight of the ISOBAM™ polymer.

The different types of ISOBAM™ polymers listed in Table 1 are all water-insoluble and have different molecular weights. ISOBAM-18 is poly(isobutylene-co-maleic anhydride) having a molecular weight of about 300,000 to 350,000 g/mol. ISOBAM-10 is poly(isobutylene-co-maleic anhydride) having a molecular weight of about 160,000 to 170,000 g/mol. ISOBAM-04 is poly(isobutylene-co-maleic anhydride) having a molecular weight of about 55,000 to 65,000 g/mol. ISOBAM-600 is poly(isobutylene-co-maleic anhydride) having a molecular weight of about 5,500 to 6,500 g/mol. ISOBAM-110 is an amide-ammonium salt of poly(isobutylene-co-maleic anhydride) having a molecular weight of about 160,000 to 170,000 g/mol.

Using Example 8 for demonstration, the solutions of Table 1 were made by the following procedure. In a 2-liter PYREX glass resin kettle reactor (5.25 inches diameter and 7 inches in height), 250 grams of ISOBAM-18 powder and 650 grams of de-ionized water were added. The reactor was equipped with an overhead motor driven blade stirrer, a thermocouple for measuring temperatures, and a liquid addition funnel. The mixture was heated by a heating mantle which was controlled by a DYNA SENSE® controller, Model 2157, supplied by Cole-Parmer Instrument Company, Chicago, Ill. The resulting mixture was stirred by a heavy-duty laboratory motor Type 6T-10, 115 volts DC, 0.6 AMP., 1/20 HP, manufactured by G. K. Heller Corp., Floral Park, N.Y. The motor was controlled by a Series S motor controller manufactured by G. K. Heller Corp. at a setting of 7 or higher. The temperature was set to 80° C. A white slurry resulted from the mixture.

A solution of sodium hydroxide was obtained by adding 71 grams of reagent grade sodium hydroxide, from Aldrich, and 350 grams of de-ionized water into a 500 ml beaker. The mixture was stirred by a magnetic stirring bar on a stirring plate.

When the temperature of mixture in the resin kettle reached the set temperature, the sodium hydroxide solution was added to the mixture dropwise through the liquid addition funnel. The mixture was again stirred at the temperature for 4 hours. A translucent solution was resulted. 8 grams of diethylenetriamine (Aldrich) was then added to the solution. The resulting solution was a solution of the liquid superabsorbent precursor.

TABLE 1

| Example No. | ISOBAM Type | Polymer Solid Content (%) | ISOBAM ™ Hydrolysis (%) | Viscosity (cps) |
|---|---|---|---|---|
| 1 | ISOBAM-18 | 10 | 55.0 | 500 |
| 2 | ISOBAM-18 | 15 | 55.0 | 2900 |
| 3 | ISOBAM-18 | 20 | 50.0 | |
| 4 | ISOBAM-18 | 20 | 52.5 | 9500 |
| 5 | ISOBAM-18 | 20 | 55.0 | |
| 6 | ISOBAM-18 | 20 | 57.5 | 11600 |
| 7 | ISOBAM-18 | 20 | 60.0 | 12400 |
| 8 | ISOBAM-18 | 25 | 55.0 | 22000 |
| 9 | ISOBAM-18 | 30 | 55.0 | |
| 10 | ISOBAM-18 | 35 | 55.0 | |
| 11 | ISOBAM-10 | 18 | 55.0 | 970 |
| 12 | ISOBAM-10 | 20 | 55.0 | 1000 |
| 13 | ISOBAM-10 | 25 | 55.0 | |
| 14 | ISOBAM-10 | 30 | 55.0 | |
| 15 | ISOBAM-10 | 35 | 55.0 | |
| 16 | ISOBAM-600 | 25 | 55.0 | |
| 17 | ISOBAM-110 | 25 | 55.0 | |
| 18 | ISOBAM-04 | 25 | 55.0 | |

Viscosity testing was done on several of the examples of Table 1. The printing resolution of the superabsorbent solutions is related to the solution viscosity. Generally, when the viscosity of the superabsorbent solutions is about 3000 to 4000 centipoise (cps) and below, printing resolution of the discrete regions is less than desired.

Figure 16:
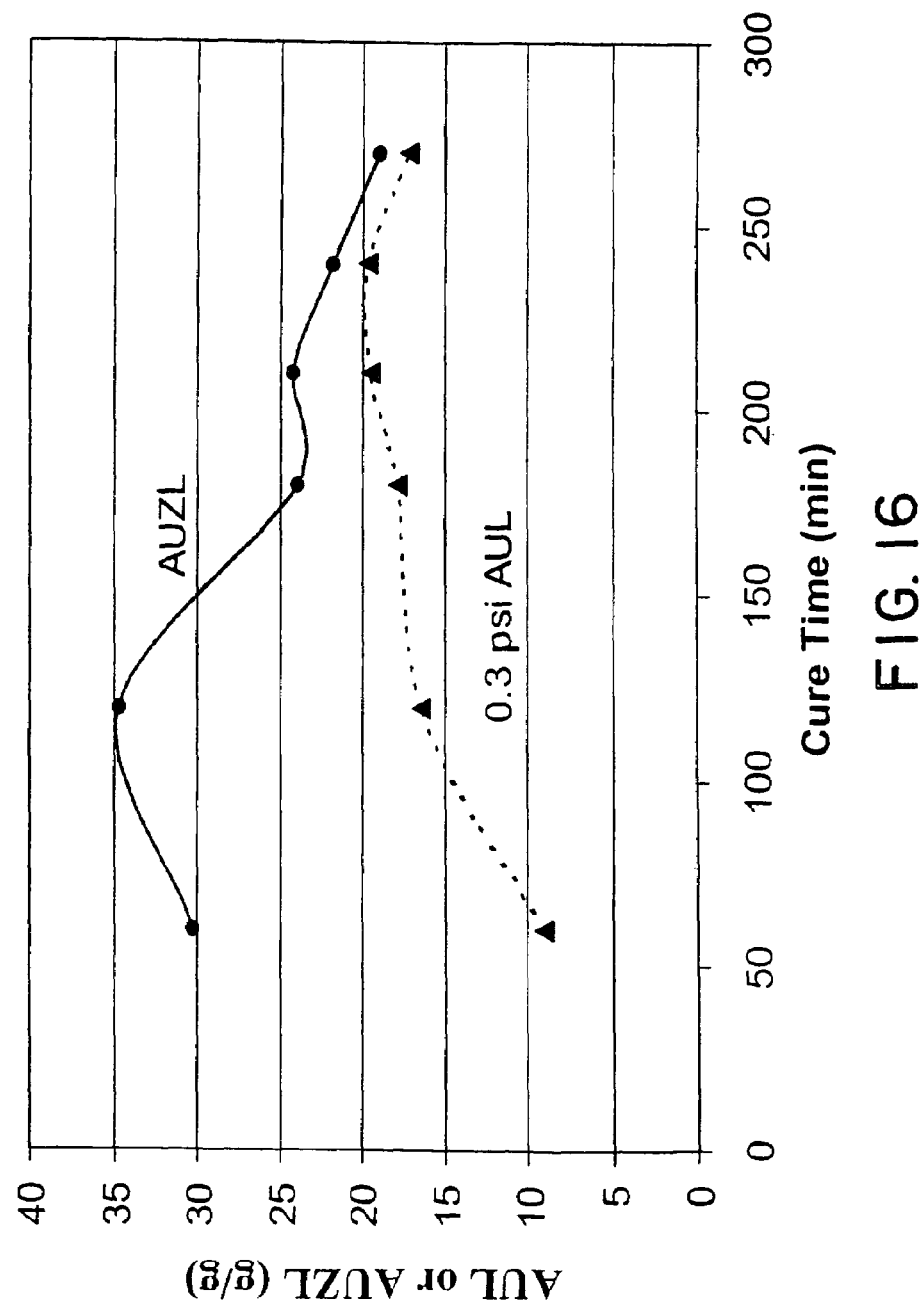
FIG. 16 is a graph of a heat curing profile of superabsorbent material according to one embodiment of the invention.

Portions of each printable superabsorbent solution of Table 1 were dried in a force-air oven at 60° C. overnight (approximately 12 hours) to remove moisture. The dried superabsorbent material was ground into particles in a blender and sieved to collect particles having a size range of about 150–600 μm. Portions of the collected superabsorbent precursor particles and different portions were each cured at 120° C. for one of 60, 120, 180, 210, 240, and 270 minutes. The portions of superabsorbent particle were then tested for both absorbency under zero load (AUZL) and absorbency under load (AUL) at 0.3 psi (pounds per square inch) using the method disclosed in U.S. Pat. No. 5,147,343, issued to Kellenberger, incorporated herein by reference. The absorbency was measured for each portion of superabsorbent and the absorbency value was plotted against the cure time to obtain a curing profile. Both AUZL and AUL were plotted as a function of time. FIG. 16 shows a representative curing profile. FIG. 16 is the curing profile plot of Example 5 and shows a peak AUL value at about 3.5–4 hours. The cure time of 3.5–4 hours at 120° C. was determined to be the optimum curing time for the superabsorbent materials. Higher curing temperatures may result in increased AUL and AUZL values due to increased efficiency in the crosslinked network formation process.

Figure 17:
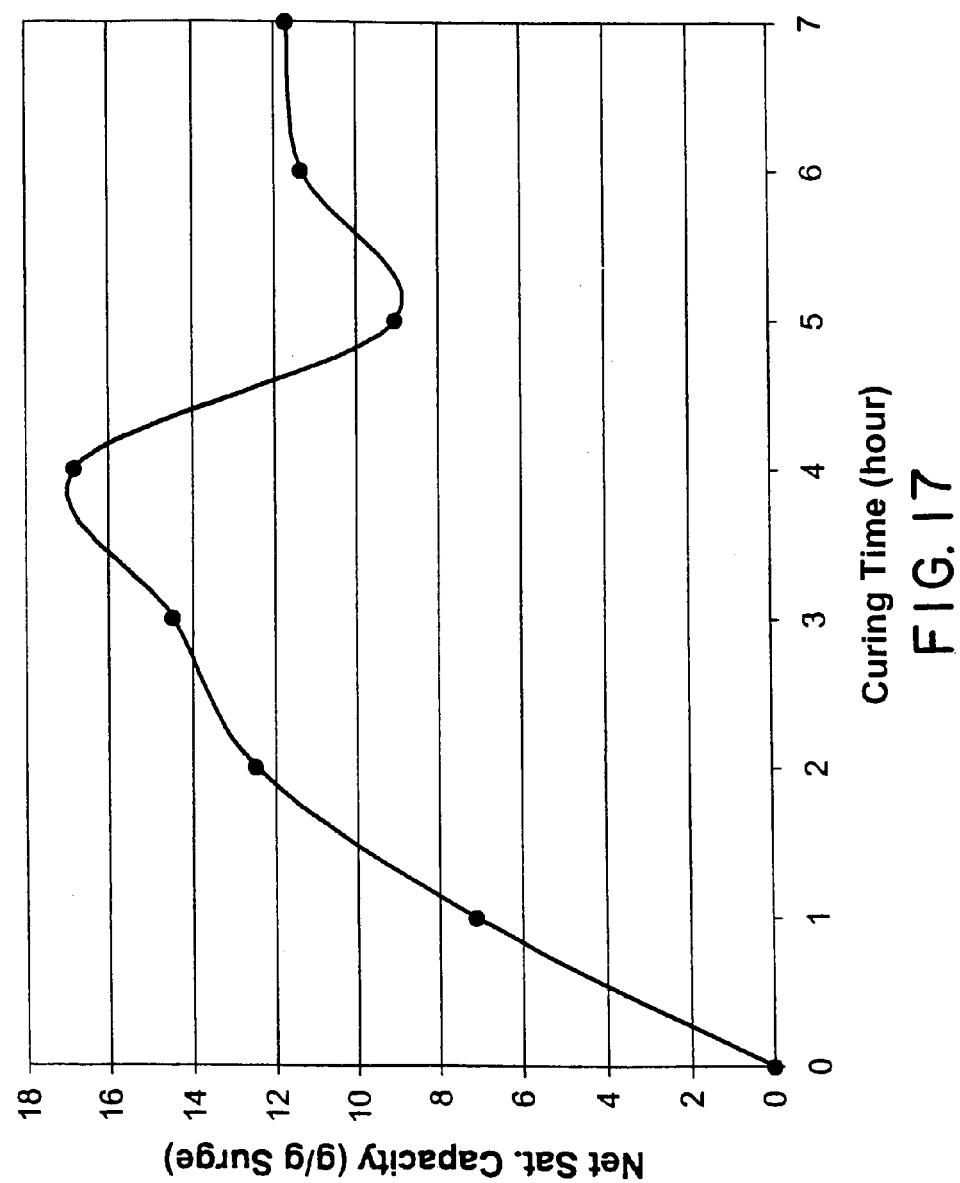
FIG. 17 is a graph of net surge capacity of superabsorbent printed surge material according to one embodiment of this invention.

The superabsorbent material solutions of Table 1 were then printed by screen printing onto surge material. The surge material was a 2.5 osy blend of 60% 3 denier per fiber (dpf) bicomponent fiber, designated as 256 from KoSa, and 40% 6 dpf bicomponent fiber designated 295, available from KoSa. Testing was then performed to determine the curing conditions that resulted in the highest absorbency. Samples of each of the wet printed superabsorbent materials of Table 1 were cured at 120° C., a curing temperature where the polyolefin surge fibers will not melt, for one of 1, 2, 3, 4, 5, 6, and 7 hours. The absorbency was then measured by saturated capacity at the various superabsorbent add-on level. "Saturation capacity" of the superabsorbent material (in grams liquid per gram superabsorbent material) is defined as the ratio of weight gain of 0.9% by weight sodium chloride solution after soaking for 20 minutes and then under pressure of 0.1 psi for 5 minutes to remove the interstitial fluid. The net saturation capacity was obtained by subtracting the saturation capacity of the surge base material from the saturation capacity of the superabsorbent printed surge material. The net increase in saturation capacity was plotted as a function of cure time. FIG. 17 shows a representative cure profile for the superabsorbent printed surge. FIG. 17 is the cure profile for Example 8, and shows that 4 hours is the optimal cure time at 120° C. for achieving the maximum saturated capacity of the superabsorbent printed surge.

Figure 18:
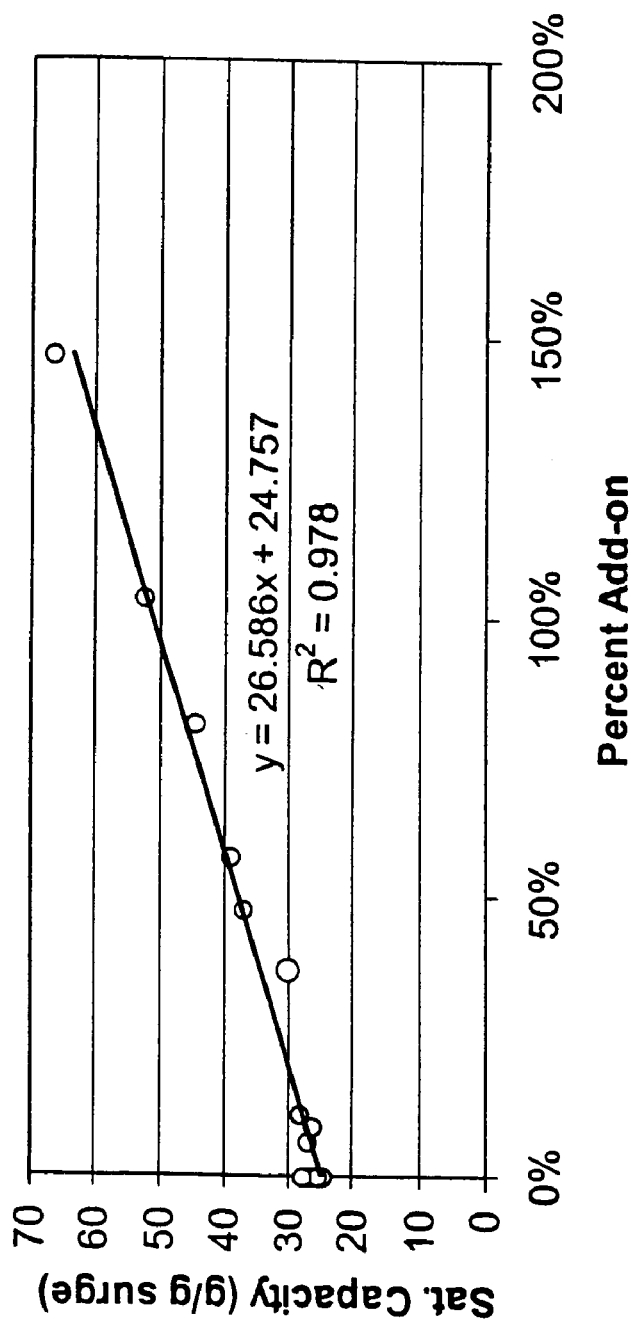
FIG. 18 is a graph showing the relationship between the amount of printed superabsorbent on surge material according to one embodiment of this invention and the saturation capacity of the resulting superabsorbent printed surge.

FIG. 18 shows a representative plot of the total saturation capacity, in grams of fluid/volume of printed surge, as a function of add-on level. FIG. 18 is the saturation capacity plot for Example 8. FIG. 18 shows that the saturation capacity of the superabsorbent printed surge increased linearly with the increase of the add-on level of the superabsorbent material. By increasing the amount of superabsorbent printed on a surge material the saturation capacity of the surge material can be increased two to three times the saturation capacity of unprinted surge material.

Figure 19:
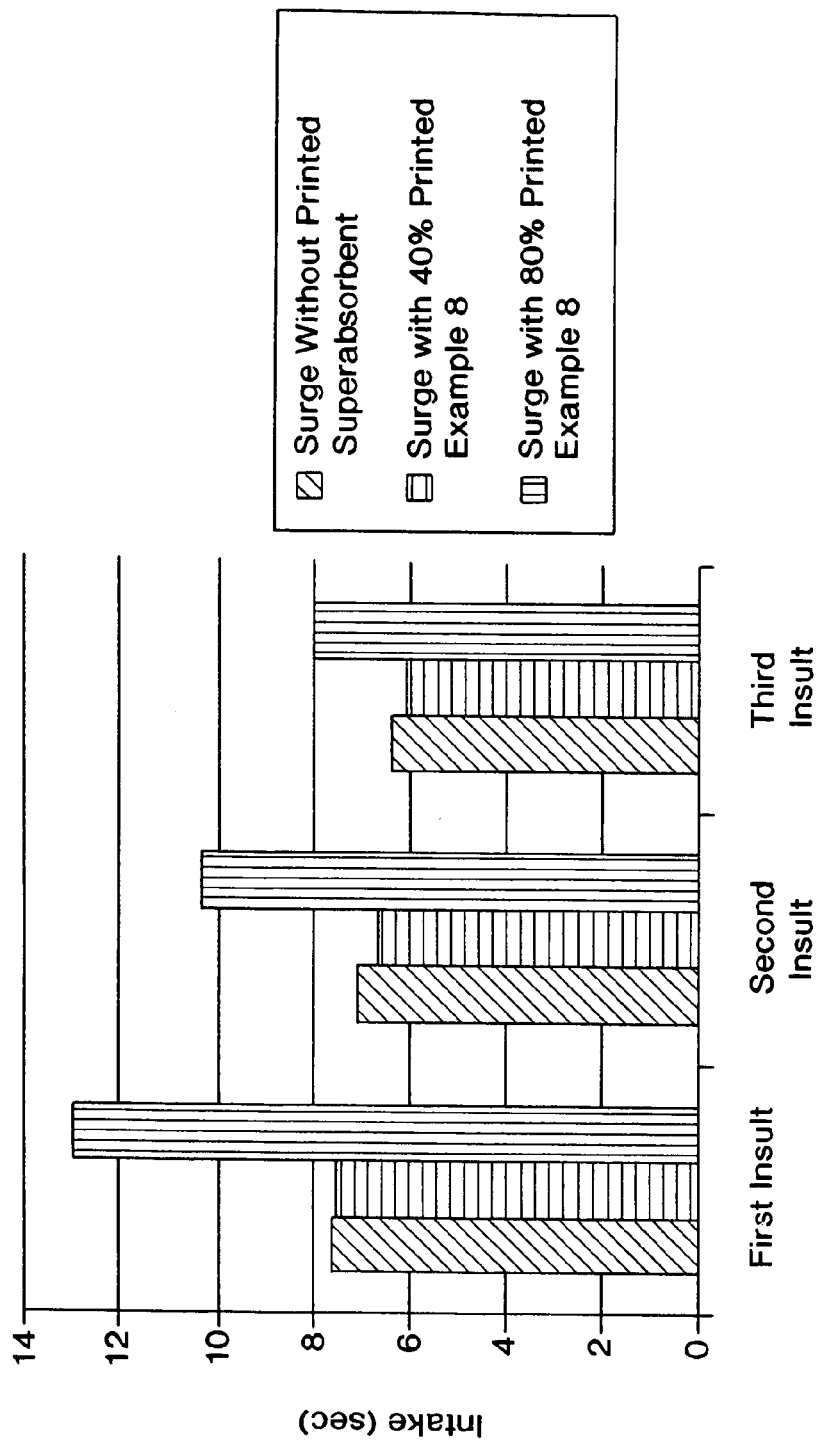
FIG. 19 is a graph plotting the intake rate of surge materials with various levels of superabsorbent against the number of insults.

FIG. 19 shows a graph of the results of an intake test to simulate urine intake in use for the sample made in Example 8. Flowback testing was performed by placing each of the example surge materials into a HUGGIES® ultrathin diaper chassis (with no absorbent core material) and placing a one inch column tube 3 inches from the top of the diaper. A 100 ml of 0.9% sodium chloride solution was poured into the tube and the intake time required for the solution to be absorbed into the diaper was recorded as the intake time for the first insult. After 15 minutes an additional 100 ml of solution was added to the cylinder and the absorption time was again recorded as the intake time for the second insult. After an additional 15 minutes another 100 ml of solution was added to the cylinder and the absorption time was again recorded as the intake time for the third insult.

A low intake time is desirable for improved/better product performance in use. FIG. 19 shows that the intake time for a surge printed with 40% of a dried crosslinked precursor of Example 8 (based on the dry weight of the surge), was about the same as without the printed absorbent for the first insult. However, the intake time was reduced for the second and third insults for the 40% printed surge. While a higher add-on level at 80% of printed and crosslinked Example 8 increased the intake time as compared to both the unprinted surge and the surge printed with only 80%, the result demonstrates that the intake time of the diaper system can be improved (or reduced) by printing an adequate amount of superabsorbent, but a high level of superabsorbent above the adequate amount is not as desirable for intake time considerations since it adversely increases the intake time of saline into the product.

Figure 20:
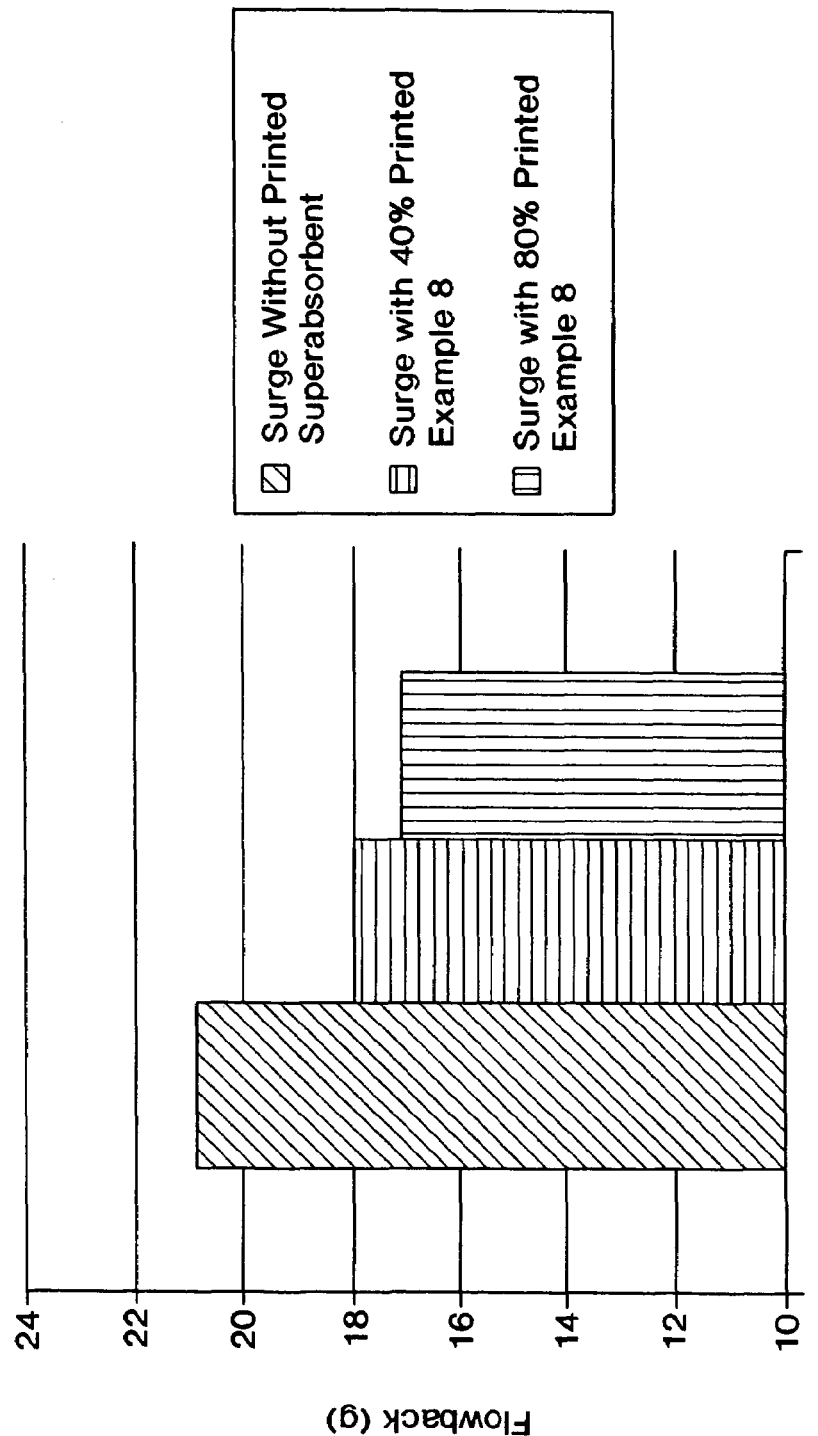
FIG. 20 is a graph plotting the amount of fluid flowback from the surge material against the amount of printed superabsorbent material.

After the third insult, each surge material was removed from the diaper chassis and placed between 2 pre-weighed blotter pages (3.5×12 inches) and a weight resulting in 0.95 psi was placed on top of the blotter paper. After two minutes the weight was removed and the blotter paper is weighed again. Flowback is the wet weight of the blotter paper minus the dry weight of the blotter paper. FIG. 20 compares amount of flowback for the control surge material, a surge material having 0.40 g printed superabsorbent material per 1.0 gram surge material (40% add-on), and a surge material having 0.80 g printed superabsorbent material per 1.0 gram surge material (80% add-on).

The results of the flowback test plotted in FIG. 20 show a decrease in fluid flowback from about 21 g to 18 g with a 40% add-on level of superabsorbent material. The fluid flowback of 80% add-on superabsorbent was even lower at 17 g. The reduction in flowback is desirable for product application of absorbent articles such as diapers to improve product performance thereby reducing leakage and skin irritation.

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. An absorbent article, comprising:
   a liquid-permeable body-side liner;
   a surge composite adjacent to the body-side liner, the surge composite comprising:
      a non-absorbent wettable fibrous surge material, the surge material having a density in a range from 0.010 to 0.100 grams per cubic centimeter;
      a plurality of discrete regions in the surge material; and
      a superabsorbent material integrally bonded to the fibers in at least some of the regions; and
   a substantially liquid-impermeable outer cover adjacent to the surge material on a side opposite the body-side liner.

2. The absorbent article of claim 1, wherein the non-absorbent, wettable fibrous surge material is a treated non-absorbent hydrophobic fibrous material.

3. The absorbent article of claim 1, wherein the discrete region has a surface area on at least one of a first surface and a second surface of the surge composite of about 5% to 80%.

4. The absorbent article of claim 3, wherein the discrete region has a surface area on at least one of the first surface and the second surface of the surge composite of about 10% to 70%.

5. The absorbent article of claim 4, wherein the discrete region has a surface area on at least one of the first surface and the second surface of the surge composite of about 15% to 60%.

6. The absorbent article of claim 1, wherein at least one of the plurality of discrete regions extends through a length of a thickness of the surge material.

7. The absorbent article of claim 6, wherein at least one of the plurality of discrete regions extends through the entire length of the thickness of the surge material.

8. The absorbent article of claim 6 wherein at least one of the plurality of discrete regions extends through about 10% to 95% of the length of the thickness of the surge material.

9. The absorbent article of claim 8, wherein at least one of the plurality of discrete regions extends through about 20% to 90% of the length of the thickness of the surge material.

10. The absorbent article of claim 6, wherein at least one of the discrete regions comprises a superabsorbent material gradient.

11. The absorbent article of claim 1, wherein at least one of the discrete regions comprises a different size.

12. The absorbent article of claim 1, wherein at least one of the discrete regions comprises a different shape.

13. The absorbent article of claim 12, wherein the discrete regions comprise at least two different shapes.

14. The absorbent article of claim 1, wherein the surge composite comprises about 1% to 400% superabsorbent add-on level based on weight of the surge material.

15. The absorbent article of claim 1, wherein the surge composite comprises about 5% to 300% superabsorbent add-on level based on weight of the surge material.

16. The absorbent article of claim 1, wherein the surge composite comprises about 10% to 200% superabsorbent add-on level based on weight of the surge material.

17. The absorbent article of claim 1, wherein the regions in which the superabsorbent material is bonded to the fibers have a plurality of microscopic pores when viewed in an X-Y plane.

18. The absorbent article of claim 17, wherein the plurality of microscopic pores have a pore size of between 50 and 500 microns.

19. The absorbent article of claim 17, wherein the plurality of microscopic pores have a pore size of between 50 and 300 microns.

20. The absorbent article of claim 17, wherein the plurality of microscopic pores have a pore size of between 50 and 200 microns.

21. The absorbent article of claim 1, wherein the superabsorbent material is bonded to the surge material by drying and crosslinking a superabsorbent precursor solution.

22. The absorbent article of claim 21, wherein the superabsorbent precursor comprises a hydrolyzed copolymer of an α-olefin, an α,β-ethylenically unsaturated organic acid anhydride or ester, and one or more of a non-polymerizable latent crosslinker.

23. The absorbent article of claim 22, wherein the nonpolymerizable latent crosslinker is selected from the group consisting of ethylene glycol, diethylene glycol, triethylene glycol, polyethelene glycol, polyvinyl alcohol, polyethylele oxide, glycerol, 1,3-propanediol, 1,4-butanediol, 1,5-pentanediol, 1,6-hexanediol, 1,8-octanediol, 1,1,1-trimethylolpropane, 1,4-butanediamine, 1,5-pentanediamine, 1,6-hexanediamine, diethylenetriamine, and analogs and derivatives thereof.

24. The absorbent article of claim 21, wherein the superabsorbent precursor comprises a hydrolyzed copolymer of isobutylene and maleic anhydride and one or more of a nonpolymerizable latent crosslinker.

25. The absorbent article of claim 21, wherein the superabsorbent precursor comprises a hydrolyzed copolymer of an α-olefin, an α,β-ethylenically unsaturated organic acid anhydride or ester, and a polyvalent metal ion crosslinker.

26. The absorbent article of claim 25, wherein the polyvalent metal ion crosslinker is selected from the group consisting of $Al^{3+}$, $Zr^{4+}$, $Fe^{2+}$, $Fe^{3+}$, $Ca^{2+}$, $Ti^{3+}$, and $Cr^{3+}$.

27. The absorbent article of claim 21, wherein the superabsorbent precursor comprises a copolymer of acrylic acid with a polymerizable latent crosslinker.

28. The absorbent article of claim 27, wherein the polymerizable latent crosslinker is selected from the group consisting of ethylene glycol allyl ether, 2-hydroxyethyl methacrylate, polyethylene glycol methacrylate, ethylene glycol vinyl ether, aminopropyl vinyl ether, and any compound having an α,β-ethylenically unsaturated group and one or more functional groups which react with a carboxyl group.

29. The absorbent article of claim 21, wherein the superabsorbent precursor comprises a polyacrylic acid and a nonpolymerizable latent crosslinker.

30. The absorbent article of claim 29, wherein the nonpolymerizable latent crosslinker is selected from the group consisting of ethylene glycol, diethylene glycol, triethylene glycol, polyethelene glycol, polyvinyl alcohol, polyethylele oxide, glycerol, 1,3-propanediol, 1,4-butanediol, 1,5-pentanediol, 1,6-hexanediol, 1,8-octanediol, 1,1,1-trimethylolpropane, 1,4-butanediamine, 1,5-pentanediamine, 1,6-hexanediamine, diethylenetriamine, and analogs and derivatives thereof.

31. The absorbent article of claim 21, wherein the superabsorbent precursor comprises a polyacrylic acid and a polyvalent metal ion crosslinker.

32. The absorbent article of claim 31, wherein the polyvalent metal ion crosslinker is selected from the group consisting of $Al^{3+}$, $Zr^{4+}$, $Fe^{2+}$, $Fe^{3+}$, $Ca^{2+}$, $Ti^{3+}$, and $Cr^{3+}$.

33. The absorbent article of claim 1, wherein the superabsorbent material is applied to the discrete regions of the surge material by one printing, spraying, and dipping.

34. The absorbent article of claim 1, wherein the surge material comprises a spunbond web.

35. The absorbent article of claim 1, wherein the surge material comprises a meltblown web.

36. The absorbent article of claim 1, wherein the surge material comprises a bonded carded web.

37. The absorbent article of claim 1, wherein the regions in which the superabsorbent material is bonded to the fibers have a layered structure with space between adjacent layers when viewed in a cross-section.

38. The absorbent article of claim 37, wherein the space between adjacent layers separates the adjacent layers by 50 to 300 microns.

39. The absorbent article of claim 37, wherein the space between adjacent layers separates the adjacent layers by 50 to 200 microns.

40. The absorbent article of claim 37, wherein the space between adjacent layers separates the adjacent layers by 50 to 150 microns.

41. The absorbent article of claim 1, wherein the superabsorbent material comprises one selected from the group consisting of hydrolyzed partially neutralized starch acrylonitrile graft copolymers, partially neutralized starch acrylic acid graft copolymers, partially neutralized saponified vinyl acetate-acrylester copolymers, hydrolyzed acronitrile copolymers, carboxymethyl cellulose, carboxymethyl starch, chitosan salts, partially neutralized polyaspartic acid, polyquartenary ammonium salts, polyvinyl amines, polyethylene imines, and combinations thereof.

42. The absorbent article of claim 1, wherein the surge material has a density in a range from 0.015 to 0.075 grams per cubic centimeter.

43. The absorbent article of claim 1, wherein the surge material has a density in a range from 0.020 to 0.050 grams per cubic centimeter.

44. The absorbent article of claim 1, wherein the surge material has a permeability in a range from 500 to 6000 Darcys.

45. The absorbent article of claim 1, wherein the surge material has a permeability in a range from 1000 to 4000 Darcys.

46. The absorbent article of claim 1, wherein the surge material has a permeability in a range from 1700 to 2500 Darcys.

47. The absorbent article of claim 1, wherein the surge material has a basis weight in a range from 0.5 to 10 ounces per square yard.

48. The absorbent article of claim 1, wherein the surge material has a basis weight in a range from 1 to 5 ounces per square yard.

49. The absorbent article of claim 1, wherein the surge material has a basis weight in a range from 1 to 3 ounces per square yard.

50. The absorbent article of claim 1, wherein the absorbent article comprises a diaper.

51. The absorbent article of claim 1, wherein the absorbent article comprises a training pant.

52. The absorbent article of claim 1, wherein the absorbent article comprises swim wear.

53. The absorbent article of claim 1, wherein the absorbent article comprises an adult incontinence garment.

54. The absorbent article of claim 1, wherein the absorbent article comprises a feminine hygiene product.

55. The absorbent article of claim 1, wherein the absorbent article comprises a medical absorbent product.

* * * * *